United States Patent [19]
Beier et al.

[11] Patent Number: 4,571,681
[45] Date of Patent: Feb. 18, 1986

[54] SWITCHING ARRANGEMENT FOR THE CONTROL OF THE CONTROL ELEMENTS OF A DENTAL TREATMENT LOCATION

[75] Inventors: Stefan Beier, Biberach an der Riss; Hermann Gmeinder, Warthausen-Oberhofen, both of Fed. Rep. of Germany

[73] Assignee: Kaltenbach & Voigt GmbH & Co., Biberach an der Riss, Fed. Rep. of Germany

[21] Appl. No.: 572,628

[22] Filed: Jan. 20, 1984

[30] Foreign Application Priority Data

Jan. 25, 1983 [DE] Fed. Rep. of Germany ....... 3302389

[51] Int. Cl.$^4$ .......................... G06F 15/42; A61C 1/02
[52] U.S. Cl. ..................................... 364/413; 433/28; 433/101
[58] Field of Search ............... 364/413, 415, 400, 180, 364/181; 433/25, 27, 28, 98, 99, 100, 101, 229

[56] References Cited

U.S. PATENT DOCUMENTS

| | | | |
|---|---|---|---|
| 4,180,812 | 12/1979 | Kaltenbach et al. | 364/413 X |
| 4,305,126 | 12/1981 | Beier et al. | 364/413 |
| 4,383,167 | 5/1983 | Gmeinder et al. | 433/27 X |
| 4,430,062 | 2/1984 | Henrichsen et al. | 433/101 X |
| 4,446,456 | 5/1984 | Beier | 364/413 X |
| 4,479,182 | 10/1984 | Beier | 364/413 |

Primary Examiner—Joseph Ruggiero
Attorney, Agent, or Firm—Scully, Scott, Murphy & Presser

[57] ABSTRACT

A switching arrangement for the control of setting or control elements which are associated with the treatment instruments of a dental treatment location, including a control data memory in which there are stored predetermined control data constants for the treatment instruments. The data is retrievable through a control component for the adjustment of the presently considered control element, and includes a first signal or voltage output arrangement which, through its supplied signals or voltages, facilitates changes in the control data which are conveyed to the control component from the control data memory. A second voltage output arrangement is connected with the control component which supplies a voltage variable from an initial or zero value, and wherein in the active switching thereof, there is prevented the receipt or delivery of signals from the control data memory and of signals or voltages from the first signal or voltage output arrangement through the control component. This renders possible the direct setting of the control elements which are associated with the dental treatment instruments from predetermined initial or zero positions, without necessitating that the signals or data, which have been currently retrieved from the control data memory, be varied in the control component.

7 Claims, 1 Drawing Figure

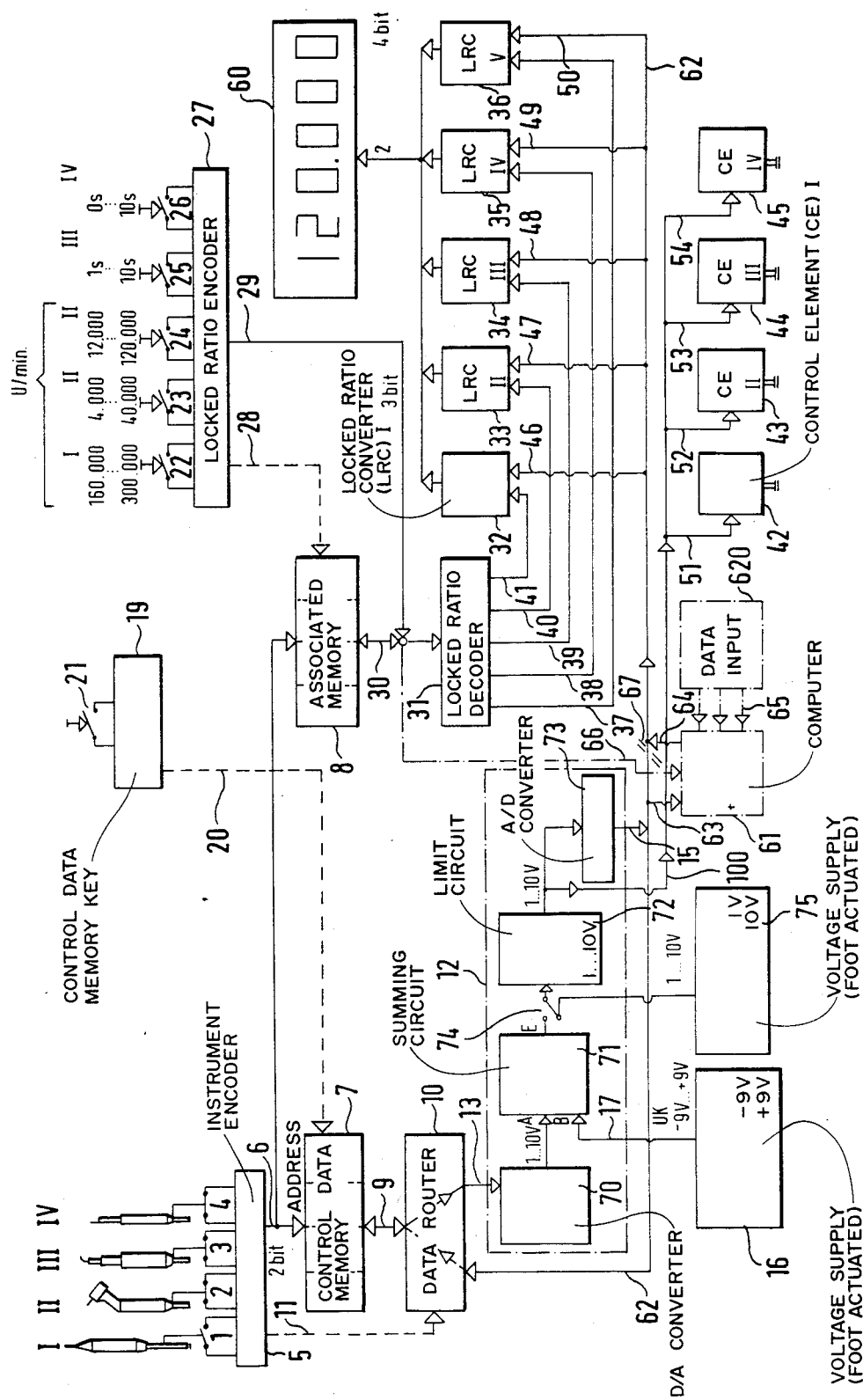

SWITCHING ARRANGEMENT FOR THE CONTROL OF THE CONTROL ELEMENTS OF A DENTAL TREATMENT LOCATION

BACKGROUND OF THE INVENTION

1. Field of the Invention

The present invention relates to a switching arrangement for the control of setting or control elements which are associated with the treatment instruments of a dental treatment location, including a control data memory in which there are stored predetermined control data constants for the treatment instruments. The data is retrievable through a control component for the adjustment of the presently considered control element, and includes a first signal or voltage emitting arrangement which, by means of its supplied signals or voltages, facilitates changes in the control data which are conveyed to the control component from the control data memory.

2. Discussion of the Prior Art

A switching arrangement of the above-described type is already known from U.S. Pat. No. 4,479,182. In this known switching arrangement, the control component converts the currently delivered control data from the control data memory into corresponding analog voltages, which are variable through the output of a desired analog voltage corresponding to a desired change, and which serve as operating signals. Due to this measure, the control data which are currently delivered from the control data memory can be varied in a relatively simple manner in correspondence with current needs. However, it has been ascertained that this switching measure will not be completely satisfactory, since it is possible to merely change the current setting or control element from an initial or zero position into operation, and to permit operation at an operating point which is proportional to the setting of a control element. Any operation in that manner will, in the known switching arrangement, necessitate that the data which have been presently obtained from the control data memory, be first so modified as to conform to the initial or zero position of the control or setting element which is to be controlled at this time, before there can be carried out the desired setting of this control element.

There is also presently known a dental treatment facility with a control data memory, as disclosed in U.S. Pat. No. 4,180,812, in which control data constants, for example, such as those for the predetermined rotational speeds of a drill machine, are stored and can be selectively retrieved by means of a control component. With the aid of this control component, there can be varied the control data by proceeding from the currently retrieved constant. Serving this purpose in the known switching arrangement is a forward-backward counter belonging to the control element, which is coupled in such a manner with a starter, that it is placed in its forward count operation or in its backward count operation, and through its count positions determines the instantaneous values of the operating data. Thereby, also in this instance, it is not possible to provide for a direct adjustment, in effect, a setting of the control elements associated with the individual treatment instruments independent of the control data currently retrieved from the control data memory.

SUMMARY OF THE INVENTION

According, it is an object of the present invention to provide a path in which a dental treatment location or facility of the above-mentioned type can be modified, while avoiding the previously described difficulties, so as to facilitate a simple setting of the current setting element from its initial or zero position.

The foregoing object is inventively achieved through a switching arrangement of the above-mentioned type in that a second voltage output arrangement is connected with the control component which supplies a voltage variable from an initial or zero value, and wherein in the active switching thereof, there is prevented the receipt or delivery of signals from the control data memory and of signals or voltages from the first signal or voltage output arrangement through the control component.

The invention provides the inherent advantage in that, in a relatively simple manner, there becomes possible a direct setting of the control elements which are associated with the dental treatment instruments from predetermined initial or zero positions, without necessitating that the signals or data, which have been currently retrieved from the control data memory, by varied in the control component.

Preferably, in a digital/analog transducer and a control component of the digital/analog transducer containing a summing circuit at the output thereof, is connected to the output of the control data memory, and the summing circuit is connected to the first signal or voltage output arrangement. The second voltage output arrangement is hereby connected with one input terminal of a selector switch device having two input terminals and one output terminal, which has its other input terminal connected with the output of the summing circuit and its output terminal connected with the setting inputs the control elements. Obtained hereby is the advantage that, in a relatively simple manner, there can be utilized a control component as is currently used in the above-considered known switching arrangement. This also provides the advantage that for the invention there can be utilized as already present control component in known dental treatment location.

In order to ensure that the signals currently delivered from the control component cannot evidence values exceeding a predetermined maximum value, which is desired and can be necessary for reasons of safety, there is preferably provided a limit circuit between the summing circuit and the setting inputs of the control elements.

The control component which is connected with the first signal or voltage output arrangement and with the second voltage output arrangement can, suitably, also be connected with a separately adjustable signal output arrangement, which delivers signals for the continual change in the control data retrieved from the control data memory. Use is made in advantageous manner of this measure when the data or signals which are contained in the control component and retrieved from the control data memory are to be subjected not only to a single correction, but when it is required that the applicable signals or data, during the period of supply of correspondingly correcting signals, are to be continually corrected. Expressed in other words, this signifies that the control component, in conjunction with the separately adjustable signal output arrangement, evidences an integral relationship with regard to the correcting signals, while in conjunction with the first-mentioned signal or voltage output arrangement, it evidences a proportional relationship with regard to the signals or voltages which are readied for the correction.

Preferably, the signal or voltage output arrangements are formed through separate operating elements of at least one foot pedal. This provides the inherent advantage of an especially simple control.

Suitably, the signal or voltage output arrangements encompass a foot pedal with a single operating element, which is actuatable either through a separate selector switch arrangement as a first signal or voltage output device, as a second voltage output device, or as a separate signal output device. Obtained hereby is the advantage that it is possible to achieve the foregoing by means of a relatively simply produceable foot pedal or actuator.

The above-mentioned foot pedal preferably incorporates an actuating element coupled with at least one potentiometer which is connectible to at least one voltage source, and which evidences a selectively actuatable or deactuatable switchable median of preferred position. Thereby it is possible to obtain a particularly simple regulation over the control component in the different types of operation.

BRIEF DESCRIPTION OF THE DRAWINGS

Reference may now be had to the following detailed description of the invention as disclosed in the accompanying single FIGURE of the drawing showing a circuit block diagram of a dental treatment location which extensively coincides with the circuit block diagram illustrated in FIG. 1 of U.S. Pat. No. 4,479,182. Thus, in the present instance there are also provided treatment instruments I, II, III and IV having switches 1, 2, 3 and 4 associated therewith, which are opened when the associated treatment instrument is withdrawn from its holder.

DETAILED DESCRIPTION

The previously mentioned switches 1, 2, 3 and 4 are connected with an instrument encoder 5 which is capable to transmit through a conductor 6 a 2-bit encompassing address which identifies that particular instrument which has just been withdrawn from its holder. The applicable 2-bit address is transmitted to a control data memory 7 as well as also to an associated memory 8. The two memories 7, 8 incorporate a number of memory or storage registers corresponding to the number of instruments, in the present instance, respectively four memory registers.

The control data memory 7 is connected through a bidirectionally employed conductor 9 with a data routing means 10 which, at one setting input receives a setting pulse through a conductor 11 from the instrument encoder 5 when one of the instruments I-IV has been withdrawn from a corresponding holder. Upon the occurrence of such a setting pulse, the data routing means 10 only completes the data path through which, from the conductor 9, there are transmitted along data signals from this data routing means 10. In the other position, the data routing means 10 transmits the data signals conveyed thereto through the conductor 9 towards the control data memory 7.

The control data memory 7 is connected through a conductor 20 with a control data memory key 19, with which there is associated a pushbutton switch 21. Through the actuation of this pushbutton switch 21, a setting pulse is transmitted through the conductor 20 to the control data memory 7. The occurrence of such a setting pulse provides the effect that a data signal or operating signal is introduceable into one of the memory registers of the control data memory 7, which is just introduced through the data routing means 10 into this memory 7.

The previously mentioned associated memory 8 is connected through a conductor 28, corresponding to one of the previously mentioned conductors 20, with a locked ratio-encoder 27, which is connected with the individual switches 22, 23, 24, 25, and 26, and through the actuation of which there can be determined for each of the individual instruments I-IV predetermined operational value ranges. These value ranges are given for the different instruments. Hereby, it is assumed that the treatment instrument I is a turbine drill, the treatment instrument II is an electric drill, the treatment instrument III is a tooth plaque remover, and the treatment instrument IV is a UV-hardener.

The locked ratio-encoder 27 is additionally connected through a connecting line 29 with a locked ratio-decoder 31 to which there is transmitted from the locked ratio-encoder 27 a locked ratio-signal corresponding to the currently actuated pushbutton of the pushbuttons 22 through 26 in the form of a 3-bit signal. This locked ratio-signal is additionally transmitted through the conductor 30 to the associated memory 8 which allows, through a setting pulse appearing on the conductor 28, this 3-bit signal to be retained in the presently addressed memory register.

Through output conductors 41, 40, 39, 38 and respectively 37, locked ratio converters 32, 33, 34, 35 and 36 are connected with the locked ratio-decoder 31, which at their output are all commonly connected with a display device 60 which allows for the introduction of presently two words of each 4-bits. For this purpose, the applicable converters 32 through 36 are actuatable through the previously mentioned conductors 41, 40, 39, 38 and 37, as well as through further conductors 46, 47, 48, 49 and 50. These last-mentioned conductors are commonly connected and receive the particular transmitted operating signals which pertain to the currently utilized treatment instrument.

The presently mentioned operating signals are transmitted from the control component 12 through a conductor 62, which is connected with the previously mentioned conductors 46 through 50 as well as with one input of the above mentioned data routing means 10. The control component 12 encompasses a digital-/analog transducer 70 which has its input connected through the conductor 30 with an output of the data routing means 10. The digital/analog transducer 70 may be so designed that it is capable of delivery at its output an output voltage of between 1 and 10 volts. This output voltage is transmitted to an input side A of a summing circuit 71, which has a further input side B connected through a conductor 17 with a voltage supply installation 16, which relates to a first voltage supply installation, and in particular encompasses a foot-operated actuator which, in its median position, delivers a voltage of zero volt, and in its end positions voltages of −9 volts or +9 volts. These voltages, which serve for the correction of the control data currently transmitted from the control data memory 7, are processed together with the analog voltage of the control data in the summing circuits 71 into a summing signal, which represents the actual operating signal for the present treatment instrument. This operating signal appears at the output side E of the summing circuit 71.

The summing circuit 71 has its output E connected at one input terminal of a selector switch 74 possessing two input terminals and one output terminal, and which has its output terminal connected with the input of a limit circuit 72, which undertakes a restriction of the voltage transmitted to the input thereof to the range of 1 to 10 volts. Hereby, in a relatively simple manner, it is possible to ensure that signals are transmitted at a voltage from the output of this limit circuit as operating signals, whose magnitude will not exceed a preset magnitude. This voltage magnitude, for example, can correspond with the analog value of the maximum value-control data signal which is contained in the control data memory.

Connected with the not yet considered input terminal of the selector switch 74 is a second voltage supply arrangement 75, which may also encompass a foot-operated actuator. With respect to this foot pedal, for example this can relate to a foot pedal starter, which is continually actuatable between a left stop and a right stop, and which thereby transmits a voltage of 1 to 10 volts. At this point, it should be remarked that in contrast with the foot pedal belonging to the voltage supply arrangement 16, this can be a pivot lever starter with a median position, from which it is displaceable towards a left stop or right stop, and into which it is always automatically returnable. Moreover, it is possible that both foot starters 16, 75 be formed by a common foot starter which incorporates a single actuating lever which can be conveyed into a definite median position through an activatable setting arrangement. Hereby connected with the applicable lever is at least one potentiometer, which is connected to at least one voltage source. With consideration being given to the relationships illustrated in the drawing, a potentiometer of that type would be actuatable through a selector switch arrangement at two different voltage sources. In this instance, the switching signals serving for the required switching over, can be the same switching signals which are also provided for actuation of the selector switch 74. At this point it is also noted that it is, however, also possible that, with the use of a single starter with a single actuating lever, to provide two separate potentiometers which are actuated through the applicable lever and which are connected to different voltage sources.

Connected to the output of the limit circuit 72 is an analog/digital transducer 73 which converts the regulating voltage (between 1 and 10 volts) transmitted thereto from the limit circuit into a corresponding digital signal. At its output, the analog/digital transducer 73 is connected through a conductor 15 with the previously above-mentioned conductor 62. Through this connection, the digital signal which is presently delivered by the analog/digital signal transducer 73, is transmitted to the locked ratio-converters 32–36, as well as to the data routing means 10.

Furthermore, a conductor 100 is connected with the output of the limit circuit 72 of the control component 12, which is connected through individual conductors 51, 52, 53, 54 with the control elements 42, 43, 44, 45, which are associated with the individual treatment instruments I–IV. Transmitted to these control elements, through the mentioned connecting conductor 100, are the analog operating signals which are currently transmitted from the limit circuit 32 for corresponding setting.

Connected to the previously mentioned conductor 15 of the analog/digital transducer 73 of the control component 12, can also be a computer 61 with an associated program memory arrangement and, if effect, through a conductor 63. This computer can, additionally, be connected through a conductor 64 with the conductor 62. In this instance, however, there is provided a separating point 67 between the input and the output of the computer 61. The computer 61 is, moreover, actuable through a conductor 66 which is connected with the above-mentioned conductors 29 and 30. For the remainder, the computer 61, which can contain a microprocessor, is connected through conductors 65 with a data input 620. The computer 61, which similar to the data input 620 need merely be optionally provided, serves the purpose that the presently prepared operating signals can be varied in accordance with the measure of further parameters (for example, in accordance with the measure of the type and size of the utilized treatment instrument).

The foregoing description of the circuit arrangement as illustrated in the drawing has indicated that the voltage supplying arrangement 75, which is designated as the second voltage output arrangement, in its actively switched state prevents the receipt or delivery of signals from the control data memory 7 and of voltages from the first voltage output arrangement 15. Hereby, it is then simply possible, in correspondence with the setting of the voltage output arrangement 75, to prepare operating data signals for the control elements which come into consideration. These operating data signals, for the remainder, can be stored in the control data memory 7 through the analog/digital transducer 73 and the data routing means 10.

Represented in the drawing is merely a first voltage output arrangement, respectively a first foot starter 16, and a second voltage output arrangement, respectively, a second foot starter 75, in connection with the control component 12; however, it is also possible that, in lieu of the first voltage output arrangement 16 there is provided a signal transmitting device as is indicated, for example, in the above-mentioned U.S. Pat. No. 4,180,812 in connection with a forward-backward counter. The applicable signal output arrangement can be connected through a digital/analog transducer with the selector switch 74. However, it is also possible to provide such a signal output arrangement in addition to the two considered voltage output arrangement 16, 75, and to connect it to a separate input terminal of the herein provided selector switch 74. Consequently, there are present a total three different capabilities for changing or, respectively, the infeed of data or signals through the control component 12.

The selection of the presently desired type of operation in the switching arrangement pursuant to the invention can be effected, for example, at the foot starter, or at the respective foot starters. In the event of the utilization of a single foot starter, which incorporates a selectively actuatable median centering of its actuating element, for the collective signal or voltage output arrangements, the actuation or, respectively, the deactivation of the median centering for the applicable actuating element can be effected through threshold value indicators; for example, through microswitches which are actuated through suitable settings of the actuating element.

Moreover, it is also possible that the respective type of operation in the switching arrangement pursuant to the invention can be controlled responsive to addresses; for example, wherein there are utilized addresses which are to be transmitted by the instrument encoder, by means of which there can be activated the individual signal or voltage output arrangement.

Finally, it is also noted that in the above considered switching arrangement pursuant to the invention, the voltage output arrangement or, respectively, the foot starter 75 need not be arranged at the input of the limit circuit 72. In contrast therewith, the voltage output arrangement or the foot starter 75 can also be connectible at the output of the limit circuit 72. In the case of the actuation of the voltage output arrangement or foot starter 75, the limit circuit can be deactivated at the input side or at the output side.

What is claimed is:

1. In a switching arrangement for the control of treatment instruments through the control elements associated with a dental treatment location, including a control data storage having control data constants stored therein for the treatment instruments through the control elements associated with a central treatment location, a control component for retrieving control data constants for the setting of a currently utilized control element, and a first voltage output means transmitting voltages to the control component for varying control data transmitted thereto from the control data memory; the improvement comprising a second voltage output means connected with the control component which provides a variable voltage between an initial value from zero and upon the actuation of which there is prevented the receipt or discharge of signals from the control data memory and of voltages from the first voltage output means through the control component.

2. Switching arrangement as claimed in claim 1, wherein said control component includes a digital to analog converter and a summing circuit connected to the output of said converter, said control component having the digital to analog converter thereof connected at the output of the control data storage and the summing circuit thereof connected to the first voltage output means, said second voltage output means being connected to an input terminal of a selector switch means having two input terminals and one output terminal, the second input terminal of said selector switch means being connected to the output of the summing circuit and the output terminal of said selector switch means being connected to setting inputs of the control elements.

3. Switching arrangement as claimed in claim 2, comprising a limit circuit being connected intermediate the summing circuit and the setting inputs of the control elements.

4. Switching arrangement as claimed in claim 1, wherein the control component is coupled to a separate adjustable signal output means which transmits signals for the continual variation of the control data retrieved from the control data memory.

5. Switching arrangement as claimed in claim 1, wherein the first voltage output means are formed through separate operating elements of at least one foot starter.

6. Switching arrangement as claimed in claim 1, wherein said first voltage output means comprise a foot starter having a single operating element, said operating element being actuatable through a separate selector switch means as the currently required signal or voltage output means.

7. Switching arrangement as claimed in claim 6, wherein said foot starter includes an actuating element coupled with at least one potentiometer connectable to at least one voltage source which includes median and preferred positions for selectively rendering the actuating element operative or inoperative.

* * * * *